United States Patent [19]

Watson et al.

[11] 4,188,946
[45] Feb. 19, 1980

[54] CONTROLLABLE PARTIAL REBREATHING ANESTHESIA CIRCUIT AND RESPIRATORY ASSIST DEVICE

[76] Inventors: Robert L. Watson, 4019 Bentway, San Antonio, Tex. 78217; Robert L. Rayburn, 12522 La Manana, San Antonio, Tex. 78233

[21] Appl. No.: 840,400

[22] Filed: Oct. 7, 1977

[51] Int. Cl.[2] .......................................... A61M 16/00
[52] U.S. Cl. .............................................. 128/204.22
[58] Field of Search ............... 128/145.5, 188, 142 R, 128/142.2, 205, 203, 194, 202, 2.08, 2.07, DIG. 17, DIG. 29

[56] References Cited

U.S. PATENT DOCUMENTS

| | | | |
|---|---|---|---|
| 2,280,050 | 4/1942 | Alexander et al. | 128/145.5 |
| 3,251,361 | 5/1966 | Rusz | 128/188 |
| 3,461,877 | 8/1969 | Morch | 128/351 |
| 3,556,097 | 1/1971 | Wallace | 128/188 |
| 3,721,238 | 3/1973 | Wise et al. | 128/188 |
| 3,814,103 | 6/1974 | Fettel et al. | 128/351 |
| 3,856,051 | 12/1974 | Bain | 137/114 |
| 3,895,630 | 7/1975 | Bachmann | 128/2.07 |
| 3,901,230 | 8/1976 | Henkin | 128/188 |
| 3,938,551 | 2/1976 | Henkin | 137/613 |
| 3,945,378 | 3/1976 | Paluch | 128/145.8 |
| 3,960,148 | 6/1976 | Dryden | 128/188 |
| 3,964,476 | 6/1976 | Palleni | 128/145.6 |
| 4,007,737 | 2/1977 | Paluch | 128/188 |
| 4,051,847 | 10/1977 | Henkin | 128/188 X |
| 4,067,330 | 1/1978 | Olsson et al. | 128/2 C |
| 4,121,578 | 10/1978 | Torzala | 128/142 R |

FOREIGN PATENT DOCUMENTS

| | | | |
|---|---|---|---|
| 1007540 | 3/1977 | Canada | 128/188 |
| 2728779 | 1/1978 | Fed. Rep. of Germany | 128/142 R |
| 419679 | 11/1934 | United Kingdom | 128/188 |
| 1270946 | 4/1972 | United Kingdom | 128/142 R |

OTHER PUBLICATIONS

Mitamura, et al, "A Dual Control System for Assisting Respiration", Medical & Biological Engineering, vol. 13. No. 6, pp. 846–854, Nov. 1975.
Mitamura, et al, "An Optimally Controlled Respirator", IEEE Transactions on Bio-Medical Engineering, vol. BME-18, No. 5, pp. 330–338, Sep. 1971.

*Primary Examiner*—Henry J. Recla
*Attorney, Agent, or Firm*—Gunn & Lee

[57] ABSTRACT

A method and apparatus for administering anesthesia to a patient is shown. A control module may be connected through an inhalation breathing circuit to a patient with a portion of the mixed/expired gases being rebreathed by the patient thus improving humidification and heat retention. By use of a $CO_2$ analyzer in the control module, the $CO_2$ content of the expired gas is accurately measured with any necessary adjustments being made in the gases delivered to the patient. The control module includes an $O_2$ analyzer, adjustable pressure warning and control device, pressure gauge, manually controlled scavenger valve, and bacterial filter connected thereto. An anesthesia ventilator or breathing bag may be used in conjunction with the control module for administering anesthesia or transportation of the patient. The inhalation breathing circuit has two concentric, non-kinking, corrugated tubes, one visually apparent within the other for delivering both fresh gas with a mixed portion of the expired gas to the patient through a special elbow adapter that allows suctioning without interrupting the fresh gas flow or ventilation of the patient.

8 Claims, 8 Drawing Figures

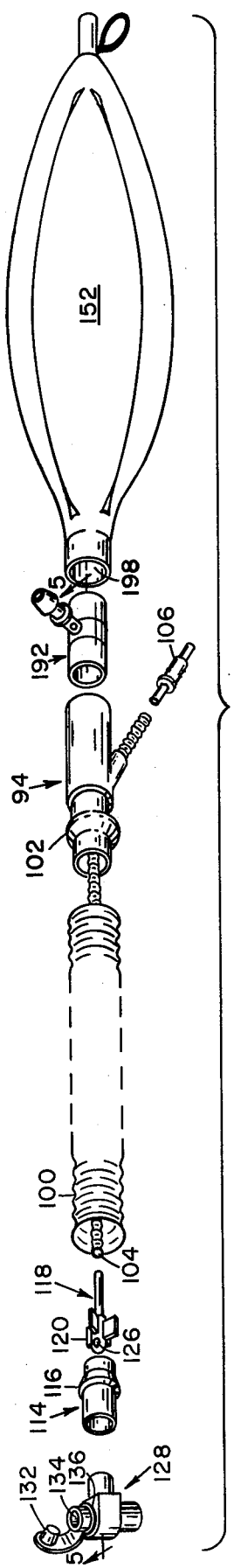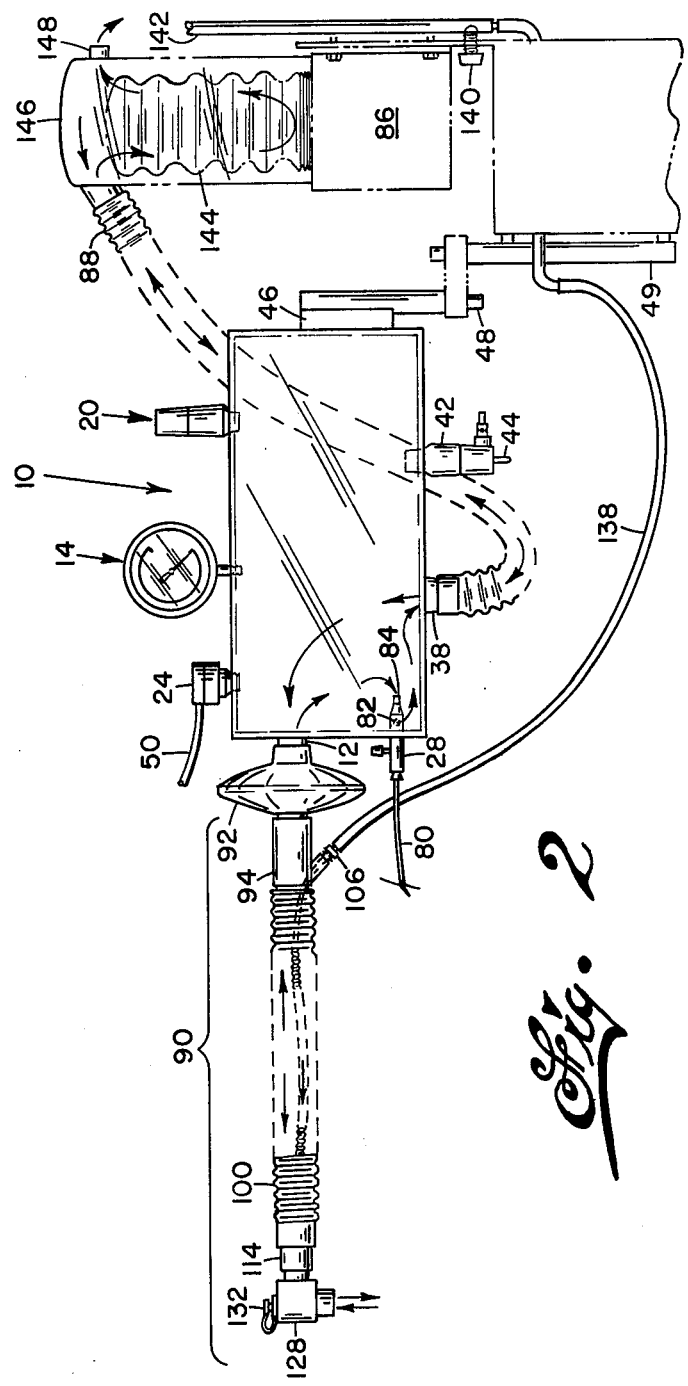
Fig. 2
Fig. 3

CONTROLLABLE PARTIAL REBREATHING ANESTHESIA CIRCUIT AND RESPIRATORY ASSIST DEVICE

BACKGROUND OF THE INVENTION

This invention relates to an anesthesia breathing circuit and respiratory care apparatus which may be used as a semi-open supply system and functions to simplify the use of the system. Numerous safety features are included as part of the system, which safety features may be used individually or in combination.

BRIEF DESCRIPTION OF THE PRIOR ART

Generally, the practice of administering anesthesia by inhalation includes two types of breathing systems. In the first, the circle carbon dioxide absorption system (semi-closed), unidirectional valving assures one-way flow of exhaled carbon dioxide and anesthesia gases through a carbon dioxide chemical absorption canister. The one-way flow prevents the rebreathing of exhaled carbon dioxide. In the second type of breathing system, a semi-open breathing circuit, a carbon dioxide absorption canister is not employed. The flow of anesthesia gases is used to remove exhaled carbon dioxide by venting exhaust gases to atmosphere. Semi-open systems have more or less universally been used either with non-rebreathing valving or have employed excessively high flow rates for incoming anesthesia gases to eliminate carbon dioxide from the breathing circuit. Prior to U.S. Pat. No. 3,856,051, both systems used more than one free swinging breathing tube to deliver the fresh anesthesia gases to the patient, and remove exhaled gases away from the patient.

In U.S. Pat. No. 4,007,737, two concentrically oriented tubes are used for delivering both inhalation and exhalation lines to and from the patient. Again, as in the older circle systems, unidirectional valving is used to allow flow only in one direction and, therefore, a greater loss of heat and humidity in the tubing occurs. Exhaust gases are vented to atmosphere after spontaneous or controlled ventilation, causing contamination of the environment, a situation which has been shown to be unhealthful.

Recent studies indicate that an anesthesia breathing circuit becomes contaminated with bacteria from the patient during administration of an anesthetic. If a ventilator is connected to the circuit, it also becomes contaminated along with the bag mount or $CO_2$ canister unless a filter is placed between the inhalation breathing circuit and the rest of the system. U.S. Pat. No. 3,856,051 does not disclose a system adaptable to present filters and, therefore, requires removal and cleaning of the ventilator as well as the breathing circuit and bag mount to prevent cross-contamination between cases.

In both of the above cited patents, a certain amount of rebreathing of exhaled gases occurs. In U.S. Pat. No. 4,007,737, the expired $CO_2$ is removed from the exhaled gases using a carbon dioxide absorber. However, both patents lack a convenient method of directly (in the circuit) determining the patient's mixed expired carbon dioxide tension. If a carbon dioxide canister (absorber) is used, then the patient's carbon dioxide is absorbed by the canister's soda lime, and is not available for mixing. If the exhaled gases are vented as in U.S. Pat. No. 3,856,051, then there is no method or opportunity for convenient measurement of carbon dioxide content.

Maintenance of near normal arterial carbon dioxide tension (normocapnia) during anesthesia is essential if the patient is to maintain near normal pulmonary ventilation to arterial perfusion ratios and normal cardiac outputs. As ventilatory tidal volumes are increased in order to prevent micropulmonary collapse during anesthesia with controlled volume ventilation, the amount of carbon dioxide removed from the patient varies in either of the previously mentioned anesthesia systems if mixed expired gases are not continuously analyzed for $CO_2$ and adjustments made. The only method available with the aforementioned patentd systems for determining the status of the patient's arterial $CO_2$ tension is by drawing a blood gas sample. This procedure carries certain risks, such as loss of a thumb or finger, and the results are delayed due to transport to and from the laboratory. Increased ventilation has caused patients to become seriously hypocapnic and has depleted the normal carbon dioxide level in their bodies. This hypocapnia has attendant dilatory effects on the pulmonary and cardiac performance. Also, large amounts of exhaled humidity and heat are lost from the anesthesia circuits. U.S. Pat. No. 4,007,737 claims to aid in the conservation of humidity by the exhalation tube enclosing the colder anesthesia inflow tube. Water content of delivered anesthesia gases is infinitesimally small. Also, placement of an exhalation unidirectional valve so close to the patent's breathing passage makes immediate rebreathing of a portion of the exhaled gases almost impossible. By the time the exhaled gases have returned from a more distant portion of the breathing circuit through the carbon dioxide absorbing canister, all humidity and heat have essentially been lost.

Control of the patient's vital functions during anesthesia and administration of gases should be accomplished with monitoring apparatus, anesthesia circuits, and breathing circuits, having as few moving (nd therefore potential malfunctioning) parts as possible. Concerning oxygen delivery, this can be monitored and controlled by oxygen analyzers in the gas delivery system to help avoid administration of hypoxic gas mixtures. Ventilation can be monitored by ventilator spirometers, ventilatory force pressure manometers, and end tidal carbon dioxide analyzers, either individually or in combination. The present invention shows that control can also be achieved during on-line monitoring of mixed expired $CO_2$ by using this value to make paired changes in inspiratory anesthesia gas/oxygen inflow rates and ventilating volumes during administration of gases.

Robert L. Rayburn, one of the co-inventors herein, recently demonstrated that since carbon dixoide production is related to body surface area, by (1) mechanically controlled anesthesia ventilation, and (2) pairing of anesthesia gas inflow with volume of ventilation, exhaled carbon dioxide concentration and arterial carbon dixoide tension can be controlled. Research with controlled partial rebreathing anesthesia techniques using a semi-open system allowed Rayburn to derive a fresh gas flow constant related to body surface area. By using three times the fresh gas flow constant for the minute ventilation delivered by mechanical anesthesia ventilator, a nearly normocapnic state in all individuals regardless of size and age was achieved. Since continuous mixing occurs, the arterial carbon dioxide tension was demonstrated to closely approximate the mixed expired carbon dioxide tension in the breathing circuit. Continuous control of the arterial carbon dioxide tension was best achieved with an in-line carbon dioxide analyzer measuring mixed expired $CO_2$ tension because, during anesthesia, ventilation may be changed or $CO_2$ production and elimination may vary, due to changes produced by surgery, anesthetics, patient's temperature, metabolism, etc. By present blood gas analysis, changes in arterial $CO_2$ must first be suspected, then a blood sample drawn, sent to the lab, a report returned, and then the correction in anesthesia fresh gas flow made. Then another sample must be drawn to assure that the correction is satisfactory. Whereas by means of an in-line $CO_2$ analyzer, variance of $CO_2$ tension and corrections of these variances may be continuously monitored.

There have been numerous incidences reported in medical journals of accidental overpressurization in semi-open and semi-closed circuits due to inadvertent closure of exhalation or pressure relief valves. This is a very dangerous situation which may cause the death of a patient. No present anesthesia system has an automatic pressure relief system and/or alarm. The present invention has an adjustable pressure relief governor with an audible alarm in addition to a combination pressure relief and scavenging valve. The adjustability of the pressure relief governor allows a lower maximum pressure to be set in the case of children versus adults, thus decreasing the risk of pneumothorax and death occuring from accidental overpressurization.

Anesthesia machines in the past have been designed with fail-safe regulators in case of loss of oxygen pressure. Recently oxygen sensors and analyzers have been used to monitor inspired $O_2$ and avoid hypoxia; however, hypoxia occuring due to system disconnects cannot be quickly diagnosed by the slow reacting oxygen analyzer. The present invention, in addition to incorporating an oxygen sensor and analyzer, incorporates a carbon dioxide analyzer with an appropriate carbon dioxide sensor (electrode). The carbon dioxide analyzer, which gives almost instantaneous results, has adjustable high and low carbon dioxide alarms so that an early warning of a circuit disconnection from a patient is given.

Previous carbon dioxide analyzing systems have been cumbersome and utilize analyzers that do not form a part of the circuit. Until recently, only end tidal $CO_2$ had been shown to correlate with arterial $CO_2$ tension. During anesthesia, measurement of end tidal $CO_2$ had not generally been used due to the complexity of the equipment and difficulty of obtaining samples at the patient's mouth during certain surgical procedures. If end tidal $CO_2$ is measured in semi-open circuits during partial rebreathing, of which the invention is an example, no correlation with arterial $CO_2$ exists. In addition, a portion of the mixed expired gases from the circuit would have to be withdrawn into the infrared analyzing chambers which, especially during pediatric anesthesia, would deplete the system of anesthetic volume. The present carbon dioxide analyzer works well on semi-open circuits, is small and portable, and forms a convenient part of the circuit thereby causing no loss of ventilating volume or change in anesthesia gas concentration.

SUMMARY OF THE INVENTION

The present invention is directed towards a controllable partial rebreathing anesthesia system and respiratory assist device having a control module connected through a breathing circuit to the patient. An exhalation and rebreathing tube forms a part of the system, which may be disposable or resterilizable, as well as a bacterial filter that may be connected thereto which filters contaminated exhaled gases. The inhalation rebreathing circuit may be connected to a transparent plastic control module. An oxygen sensor, carbon dioxide sensor, pressure relief governor, ventilator force manometer, exhalation and scavenging valve, and anesthesia reservoir bag or mechanical anesthesia ventilator may be connected to the control module for greater safety and efficiency. The patient's ventilation is monitored and the patient's carbon dioxide state is continuously determined by the carbon dioxide sensor, therefore allowing lower fresh gas flows to be used safely. This insures greater rebreathing of mixed expired gases. The greater rebreathing improves heating and humidification of the inspired gases which is not obtained by prior systems. The carbon dioxide analyzer aids both in the control of ventilation and in diagnosing abnormal patient carbon dioxide states. The inhalation breathing circuit by virtue of its adaptability to resuscitative equipment can be disconnected from the control module and used in the transporation of patients requiring supplemental oxygen, ventilation, end-expired pressure breathing, and tracheal suctioning.

For greater safety, a non-kinking corrugated tube, which may be disposable or resterilizable, is used as the fresh gas flow line and is connected to the anesthesia machine flow tube externally where the integrity of the connection can be visually seen to avoid undetected disconnection. In addition, the fresh gas is delivered at the patient end in a radial fashion at right angles to both the patient and the fresh gas and exhalation tubes. Such a delivery not only conserves the exhaled humidity by giving a cool circumferential screen of gas into which the patient exhales thereby causing a condensing of humidity at the patient end, but prevents venturi gas flows which create a vacuum in the exhalation tube and may be dangerous in certain patients.

The present invention attempts to prevent bacterial contamination of the control module and ventilator with exhaled gases by allowing use of an anesthesia bacterial filter at the connection of the exhalation tube and the control module.

The control module is small and lightweight aiding in its transportability. All external parts may be removed, and the plastic module and the component parts sterilized. All of the component parts of the control module can be externally visualized due to the transparent plastic from which the control module is made. A control valve that may be externally adjusted is connected to the control module to allow a graduated venting of the exhaled gases and scavenging thereof. The exhalation/-scavenging valve is located immediately adjacent to the ventilating reservoir bag for ease of operation.

The inhalation breathing circuit is designed so that it may be removed from the control module, and an exhaust control valve and/or anesthesia reservoir bag may be connected to the filter end. The circuit may be used with a transport oxygen tank for transportation of the patient from one location to another. During transportation, positive end expiratory pressure can be maintained (via adaptability to a Carden valve), which is critical when transporting small children who have been on artifical respiratory devices to provide end expiratory pressurization.

An endotracheal tube elbow adapter is provided with a stoppered and sealed evacuation portal, the top of which may be removed to allow tight fitting suction tubes and/or flexible bronchoscopes to pass into the endotracheal tube and trachea for diagnosis and/or removal of secretions while maintaining volumetric pressure and oxygenation of the system.

The carbon dioxide analyzer includes an electrode inserted in the control module to measure the carbon dioxide tension and give an electrode signal proportionate thereto. The electrode signal is then converted in an analyzer circuit to a control signal that is inversely related to fresh gas flow, including an adjustment factor to account for normal variations between carbon dioxide tension in the patient and that of the control module. By adjusting the fresh gas flow, a reciprocal change in the carbon dioxide tension is demonstrated.

BRIEF DESCRIPTION OF THE DRAWINGS

FIG. 2 is an elevated side view of the present invention being used with an anesthesia ventilator and anesthesia machine.

FIG. 3 is an exploded perspective view of a respiratory assist device.

DESCRIPTION OF THE PREFERRED EMBODIMENT

Figure 1:
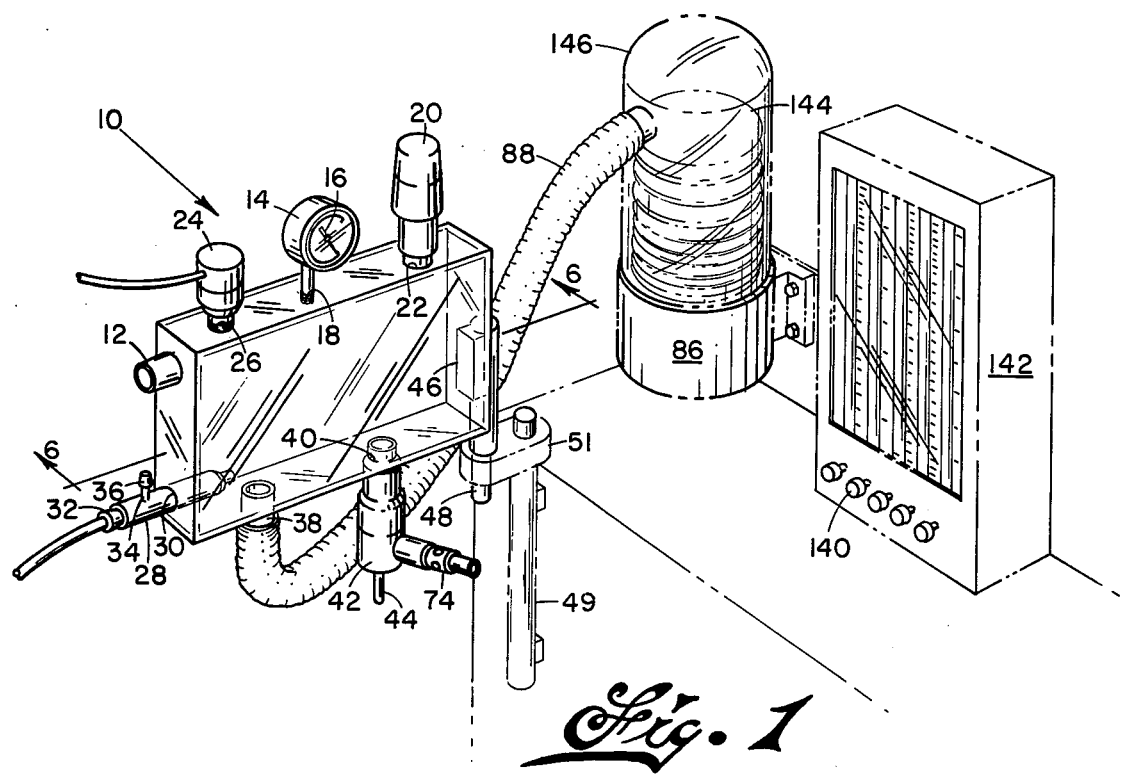
FIG. 1 is a perspective view of a control module with some attachments.

Referring to FIG. 1 of the drawings, a control module designed by reference numeral 10 is shown. The control module 10 is one of the major components of the hereinafter described control partial rebreathing anesthesia system or circuit. While the control module 10 may be made from any suitable substance, in this preferred embodiment, the control module 10 is made from a clear heavy-duty plastic wherein internal portions are clearly visible.

The control module 10 has a number of items that may be connected thereto. The exhaled or expired gases normally feed into the control module 10 through flanged opening 12. Exhaled or expired gases received inside of the control module 10 may be regulated or monitored therein. A pressure gauge 14 with a pressure indicator 16 connects to the control module 10 through opening 18 to continually monitor the pressure inside control module 10. A pressure relief governor/alarm valve 20 is connected through opening 22 to the control module 10 to prevent and warn of overpressurization. An audible alarm and relief of pressure is given by the pressure relief governor/alarm valve 20 when the maximum pressure set for the control module 10 has been exceeded.

The expired gases received by the control module 10 are also monitored by an oxygen sensor 24 which connects to the control module 10 through opening 26. Also, a carbon dioxide electrode is inserted inside of elongated housing 28 which is in turn inserted in opening 30 of the control module 10. The carbon dioxide electrode (not shown in FIG. 1) is held inside of the elongated housing 28 by means of stopper 32. For calibration of the carbon dioxide electrode as will be explained in more detail subsequently, an auxiliary conduit 34 connects by one end thereof to the inside of the elongated housing 28. The opposite end of the auxiliary conduit 34 is normally covered by cap 36 after calibration has been completed.

Mounting flange 38 may be connected to an anesthesia reservoir bag or ventilator tubing leading to and from an anesthesia mechanical ventilator 86. Opening 40 receives an exhalation/scavenger valve 42 therein. By means of stem 44, the exhalation/scavenger valve 42 may be closed, partially opened, or fully opened. Operation of the exhalation/scavenger valve 42 will be explained in more detail subsequently.

The control module 10 may have a mounting fixture 46 either removably or permanently connected thereto by any suitable means. In this preferred embodiment, the mounting fixture 46 is formed as part of the control module 10 for connecting the control module 10 to a standard anesthesia machine mounting pole 49 by means of a pivot axis 48. Connecting bar 51 pivotally connects the pivot axis 48 to the mounting pole 49.

Figure 6:
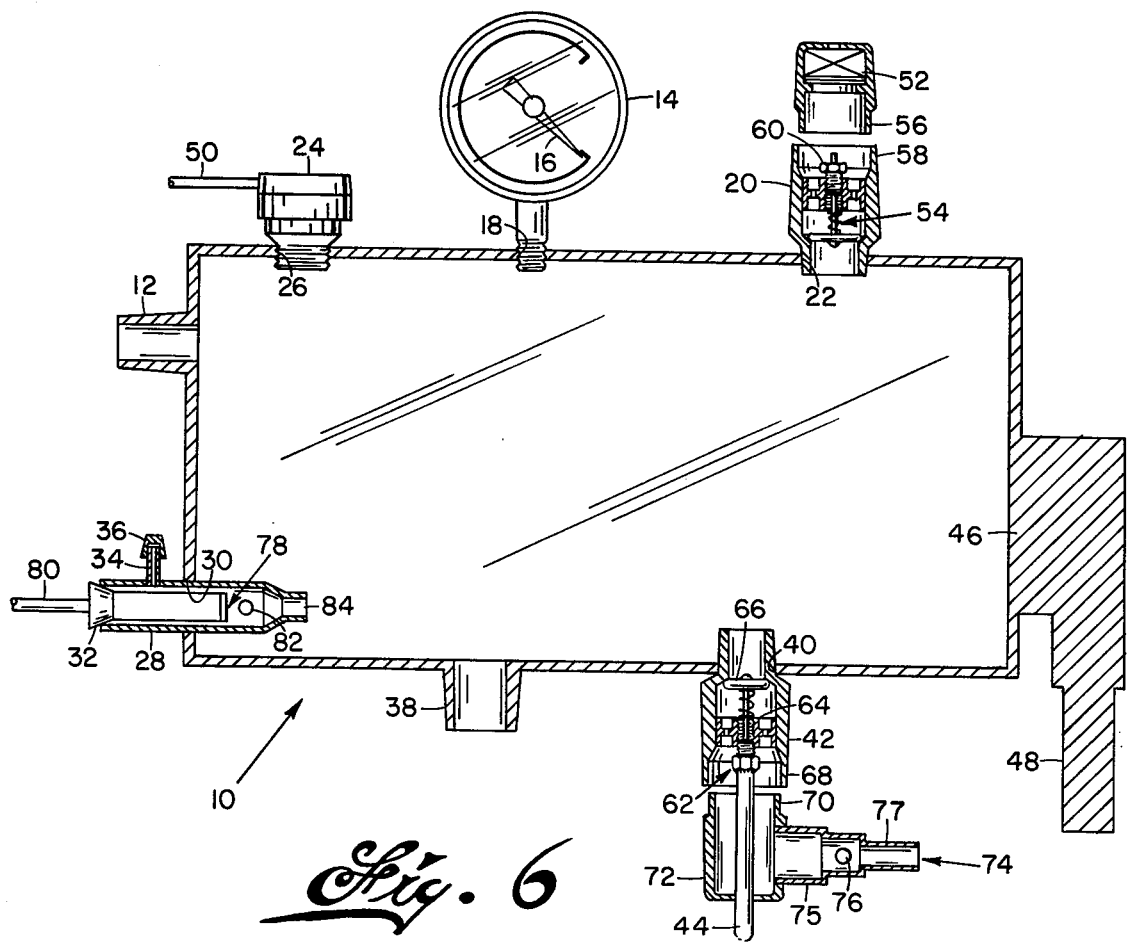
FIG. 6 is a cross-sectional view of the control module shown in FIG. 1 taken along section lines 6—6.

Referring now to FIG. 6 of the drawings, a cross-sectional view of the previously described control module 10 is shown. As can be seen in FIG. 6, the openings 26 and 18 have threads therein for receiving the oxygen sensor 24 and pressure guage (also called manometer) 14 therein, respectively. The oxygen sensor 24 is connected to a suitable oxygen analyzer by means of electrical connection 50. A typical oxygen sensor 24 with appropriate analyzer is manufactured by BioMarine Industries located in Devon, Pennsylvania, and commonly referred to as "Oxygen Analyzer 202R". Other types of oxygen analyzers are also commercially available.

The pressure relief governor/alarm valve 20 has a reed alarm 52 to give an audible alarm if pressurized gases flow around the valve element 54. Flange 56 of the read alarm 52 is securely received inside a flange 58 for a tight connection therewith. The pressure level at which the valve element 54 of the pressure relief governor/alarm valve 20 will allow gas to flow therethrough, which is continuously indicated by the pressure indicator 16 of pressure gauge 14, can be adjusted by removing the reed alarm 52 and adjusting nut 60 of the valve element 54. Naturally, pressure levels for a small child should be set for a lower value than pressure levels for an adult.

The exhalation/scavenger valve 42 has an adjustable valve element 62 with stem 44 threadably connected inside of valve body 64. The adjustment of the stem 44 opens and closes the valve seal 66. Exhaled or expired gases from a patient that flow through the exhalation/scavenger valve 42 also flow through mating flanges 68 and 70 into collecting cap 72. The collecting cap 72 has a graduated venting tube 74 with radial openings 76 located therein. A large reservoir tube may be connected to the large diameter portion 75 of the graduated venting tube 74. A vacuum line is normally connected to the small diameter portion 77 of the graduated venting tube 74. By having the radial openings 76 inside of the large reservoir tube helps prevent the vacumm line from decreasing the pressure inside of the control module 10 below a predetermined level as will be subsequently explained.

Referring now to the elongated housing 28 in opening 30 as shown in FIG. 6, the $CO_2$ electrode 78 is pictorially shown therein. In normal operation, the $CO_2$ electrode 78 is shoved inside of elongated housing 28 until stopper 32 seals with the end thereof. Thereafter, cap 36 is removed and a predetermined percent $CO_2$ gas is connected through auxiliary conduit 34 to the elongated housing 28. The percentage of the $CO_2$ gas inside of housing 28 is sensed by the $CO_2$ electrode and transmitted to the $CO_2$ analyzer circuit (as will be described subsequently) through electrical connection 80. An adjustment is made in the analyzer circuit to give the correct, predetermined output indicating the correct carbon dioxide tension. This procedure may be repeated for a different percentage $CO_2$ gas to complete initial calibration of the $CO_2$ analyzer. After disconnection of the predetermined percentage $CO_2$ from the auxiliary conduit 34 and replacing cap 36, upon use of the $CO_2$ electrode 78 as part of an anesthesia breathing circuit, the exhaled gases received inside of the control module 10 will flow through radial openings 82 and end opening 84 to come in contact with the $CO_2$ electrode 78. The signal generated by the $CO_2$ electrode 78 is fed through electrical connection 80 to the analyzer circuit.

Referring now to FIG. 2 of the drawings, a complete anesthesia breathing circuit is shown wherein the control module 10 is connected to a mechanical ventilator 86 by means of ventilator delivery hose 88 connected to mounting flange 38. Also connected to the flanged opening 12 is an inhalation breathing circuit 90 and bacterial filter 92.

Figure 5:
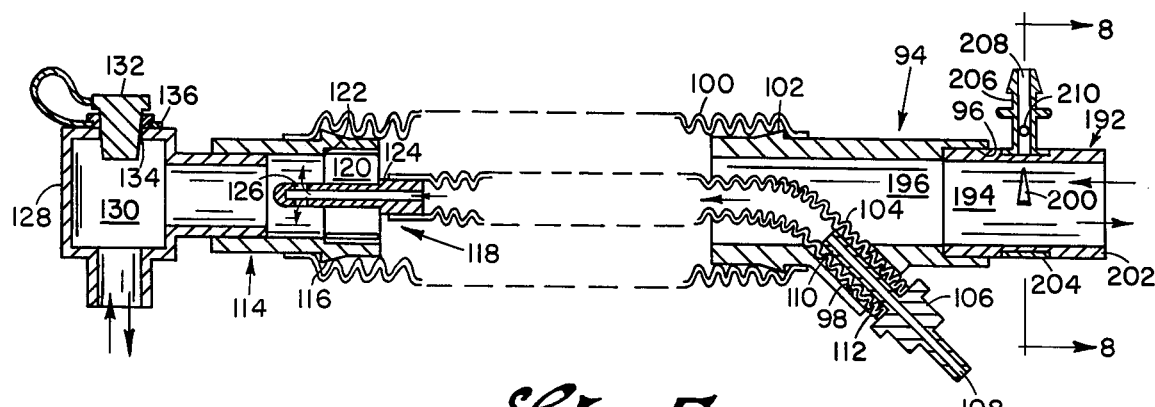
FIG. 5 is a cross-sectional view of FIG. 3 taken along section lines 5—5.

Referring to FIGS. 3 and 5 in conjunction with FIG. 2, the inhalation breathing circuit 90 will be explained in more detail. A bacterial filter 92 is connected to the flanged opening 12, which bacterial filter 92 allows air flow therethrough in either direction. The bacterial filter 92 may be received inside of large opening 96 of circuit connector 94, or may have an exhaust control valve 192 therebetween as will be explained subsequently. Circuit connector 94 has a small opening 98 which extends outward from its longitudinal axis at approximately 30°. The end of the circuit connector 94 opposite the bacterial filter 92 shown in FIG. 2 or opposite the exhaust control valve 192 shown in FIGS. 3 and 5 is received inside of a large corrugated plastic tube 100. A ridge 102 around the outer edge of the circuit connector 94 helps maintain the large corrugated plastic tube 100 thereon. Extending through the small opening 98 is a small corrugated plastic tube 104 which receives a fresh gas line adapter 106 in one end thereof. The fresh gas line adapter 106 has a passage 108 therethrough with a small diameter portion 110 being received inside of small corrugated plastic tube 104. When the fresh gas line adapter 106 is inserted inside of the small corrugated plastic tube 104, both of which are subsequently inserted inside of the small opening 98, compressed corrugations 112 are clearly visible to show a good connection between the fresh gas line adapter 106 and the small corrugated plastic tube 104. A bonding compound could be further applied if desired to insure a good connection between the small corrugated plastic tube 104 and the fresh gas line adapter 106.

The small corrugated plastic tube 104 extends inside of the large corrugated plastic tube 100 to an expiratory mixing tube connector 114. One end of the expiratory mixing tube connector 114 is received inside of large corrugated plastic tube 100. Ridge 116 around expiratory mixing tube connector 114 helps maintain a good airtight connection with the large corrugated plastic tube 100. Inside of the expiratory mixing tube connector 114 is a fresh gas flow line delivery adapter 118 which has radial flanges 120 resting against internal shoulder 122 of expiratory mixing tube connector 114. A center tube 124 of the delivery adapter 118 is connected to the small corrugated plastic tube 104 for receiving fresh gases therefrom. The connection may be secured by any suitable means, such as bonding. Fresh gases traveling through center tube 124 of the delivery adapter 118 are radially discharged from side ports 126. Additionally, an end port may be included in the delivery adapter 118. This insures a mixing of the fresh gas delivered through the small tube 104 with the expired/exhaled gases from the patient in the large corrugated plastic tube 100.

The expiratory mixing tube connector 114 connects to an elbow adapter 128. The elbow adapter 128 may connect to an endotracheal tube or a face mask of the patient. The elbow adapter 128 has a passage 130 therein which changes the direction of flow of the inhaled/exhaled gases by 90°. If the elbow adapter 128 is connected to an endotracheal tube located in a patient, suctioning or bronchoscopic observation of the patient's lungs may be necessary. By removing plug 132 from upper opening 134, suctioning or bronchoscopic observation of the patient can be accomplished while other respiratory functions are being performed. By the proper sizing of the upper opening 132, an essentially airtight connection with the suctioning tube or bronchoscope is possible. The airtight connection further insures the performing of suctioning or bronchoscopic observation without loss of anesthesia and/or respiratory care functions. The plug 132 has a retaining ring 136 connected to elbow adapter 128 to insure that the plug 132 remains adjacent to upper opening 134 thereby preventing delays in opening or closure thereof.

Referring back to FIG. 2, assume that the elbow adapter 128 is connected to the endotracheal tube of a patient. The fresh gas line adapter 106 is also connected to fresh gas line 138. The fresh gas line 138 may be delivering gases and/or oxygen to the patient at a relatively low pressure. The fresh gas line 138 is connected through a metering valve 140 to a supply line control 142. Assuming that the mechanical ventilator 86 is being used, bellows 144 will be operating in an up and down manner.

As the patient breathes through the endotracheal tube connected to the elbow adapter 128, fresh gas is delivered through the side ports 126 of the delivery adapter 118 and is mixed with gases contained in the large corrugated plastic tube 100. Therefore, as the patient breathes in, not only will the patient receive fresh gas from the small tube 104, but will rebreathe a portion of the gases contained in the large tube 100. Flow of the gases through the small tube 104 is continually in the direction as indicated by the arrow. However, flow through the large tube 100 will be partially oscillatory with the general direction of movement of the gases therein as determined by the flow rate through the small tube 104 and will be toward the control module 10.

As the mixed expired gases are received in the control module 10, the expired gases will flow through radial opening 82 and end opening 84 into the elongated housing 28 containing the $CO_2$ electrode. The $CO_2$ electrode 78 will measure the carbon dioxide content of the mixed expired gases and send a control signal through electrical connection 80. Also, exhaled gases received in the control module 10 would flow in a general direction through ventilator delivery hose 88 into ventilator bellows 144. Motion of the bellows 144 in the ventilator chamber 146 allows the discharge of a portion of the expired gases therein out of discharge opening 148. The discharge opening 148 has a one-way valve located therein to insure one-way flow therethrough as indicated by the arrows. Another controllable portion of gases is discharged by the bellows 144 into the control module 10 via ventilator delivery hose 88 toward the patient for rebreathing through the large corrugated plastic tube 100.

In the system as shown in FIG. 2, the exhalation/scavenger valve 42 is closed. However, pressure manometer 14 continually monitors the pressure of the gas being delivered to the patient and pressure relief governor/alarm valve 20 is included for the patient's further safety. The pressure relief governor/alarm valve 20 is adjusted to a predetermined maximum pressure in the manner previously described. Simultaneously, oxygen sensor 24 generates an electric signal which represents the oxygen content of the mixed expired gases. Bacterial filter 92 helps insure that all expired gases that reach the control module 10 do not contaminate the control module 10 with the patient's bacteria, and any bacteria in the control module 10 will not be transmitted to the patient.

By use of the system as described in FIG. 2, each time the patient inhales, a portion of the gas inhaled by the patient is received from the fresh gas line 138 and a portion will be received from the large tube 100. The amount of fresh gases breathed during each inhalation is regulated by the flow through the fresh gas flow line 138. The amount of oxygen delivered to the patient can be accurately controlled by adjusting metering valve 140. The patient will rebreathe only a portion of the exhaled gases during each breath.

Figure 4:
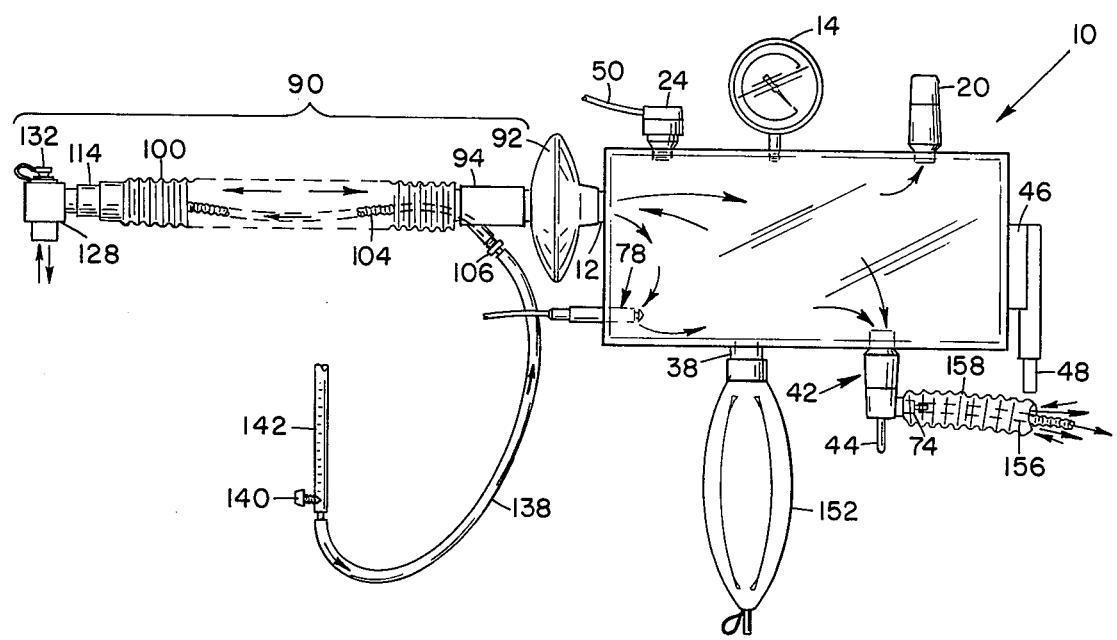
FIG. 4 is an elevated side view of the present invention being used with an adjustable exhalation/scavenging valve and an anesthesia reservoir bag.

Referring now to FIG. 4 of the drawings, the control module 10 is shown in an alternative connection. The inhalation breathing circuit 90 is again connected to either a face mask or an endotracheal tube by means of the elbow adapter 128. Again, the small tube is received inside of the large tube 100 as previously described through the fresh gas line adapter 106 and circuit connector 94. Fresh gas, which may include anesthesia gases and/or oxygen, is again supplied through the fresh gas line 138, metering valve 140 and fresh gas supply line control 142. The bacterial filter 92 is located between the circuit connector 94 and mounting flange 12 of control module 10. The oxygen sensor 24 again analyzes the oxygen content of the mixed expired gases received in the control module 10, and the pressure gauge 14 monitors the pressure. The pressure relief governor/alarm valve 20 provides a maximum pressure limit for the exhaled gases inside of control module 10. If the pressure inside of the control module 10 exceeds the pressure set in the pressure relief governor/alarm valve 20, the pressure will automatically be relieved and an audible alarm will be given. Changes in the anesthesia breathing circuit as shown in FIG. 4 include the elimination of elongated housing 28 so that the $CO_2$ electrode 78 is inserted directly into the control module 10. A tight seal between the $CO_2$ electrode 78 and the opening 30 prevents the escape of mixed expired gases from the control module 10.

Mounting flange 38 has an anesthesia reservoir bag 152 connected thereto into which monitored mixed expired gases flow bidirectionally from control module 10 to reservoir bag 152. Movement of mixed expired gases from the reservoir bag 152 may be either spontaneous in the breathing patient or assisted/controlled by manual compression of the reservoir bag 152 in the respiratorally depressed or paralyzed patient. In either condition, a portion of the mixed expired gases is either drawn or forced during inspiration in the direction of the patient sequentially through flange 38 into control module 10, through flange 12, through filter 92 and finally through inhalation breathing circuit 90 to the patient. Normally, the overflow expired gases flow from the control module 10 via exhalation/scavenger valve 42. The amount of flow through exhalation/scavenger valve 42 is controlled by the adjustment of stem 44. By connection of a vacuum line 156 to the small portion of graduated venting tube 74, a vacuum is created inside of exhalation/scavenger valve 42 to remove expired gases from control module 10. To avoid creating excessive vacuum inside of the control module 10, the vacuum line 156 may draw air from a large vent/scavenger line 158 through openings 76. Also, the large vent/scavenger line 158 may be used without the vacuum line 156 to remove expired gases.

In operation, the circuit as shown in FIG. 4 supplies fresh gas and/or anesthesia gases to the patient via fresh gas line 138, small tube 104 and elbow adapter 128. By regulating the flow through the fresh gas line 138 by metering valve 140, the amount of expired gases that are rebreathed can be controlled. Again, expired gases, while having some oscillatory motion inside of large tube 100, generally flow through the bacterial filter 92 into the control module 10. The oxygen sensor 24 determines the oxygen content of the mixed expired gases and the pressure gauge 14 gives an accurate reading of the pressure inside of control module 10. The safety feature of the pressure relief governor/alarm valve 20 is again adjusted to the individual patient. The $CO_2$ electrode 78 continually monitors the carbon dioxide tension of the mixed expired gases. The amount of fresh gas delivered to the patient is regulated according to the reading received from the carbon dioxide electrode 78 in a manner as will be subsequently explained. By opening the exhalation/scavenger valve 42 by means of stem 44, exhaled gases are removed from the control module 10 either by vacuum line 156, by a large vent line 158, or by a combination of both.

Figure 7:
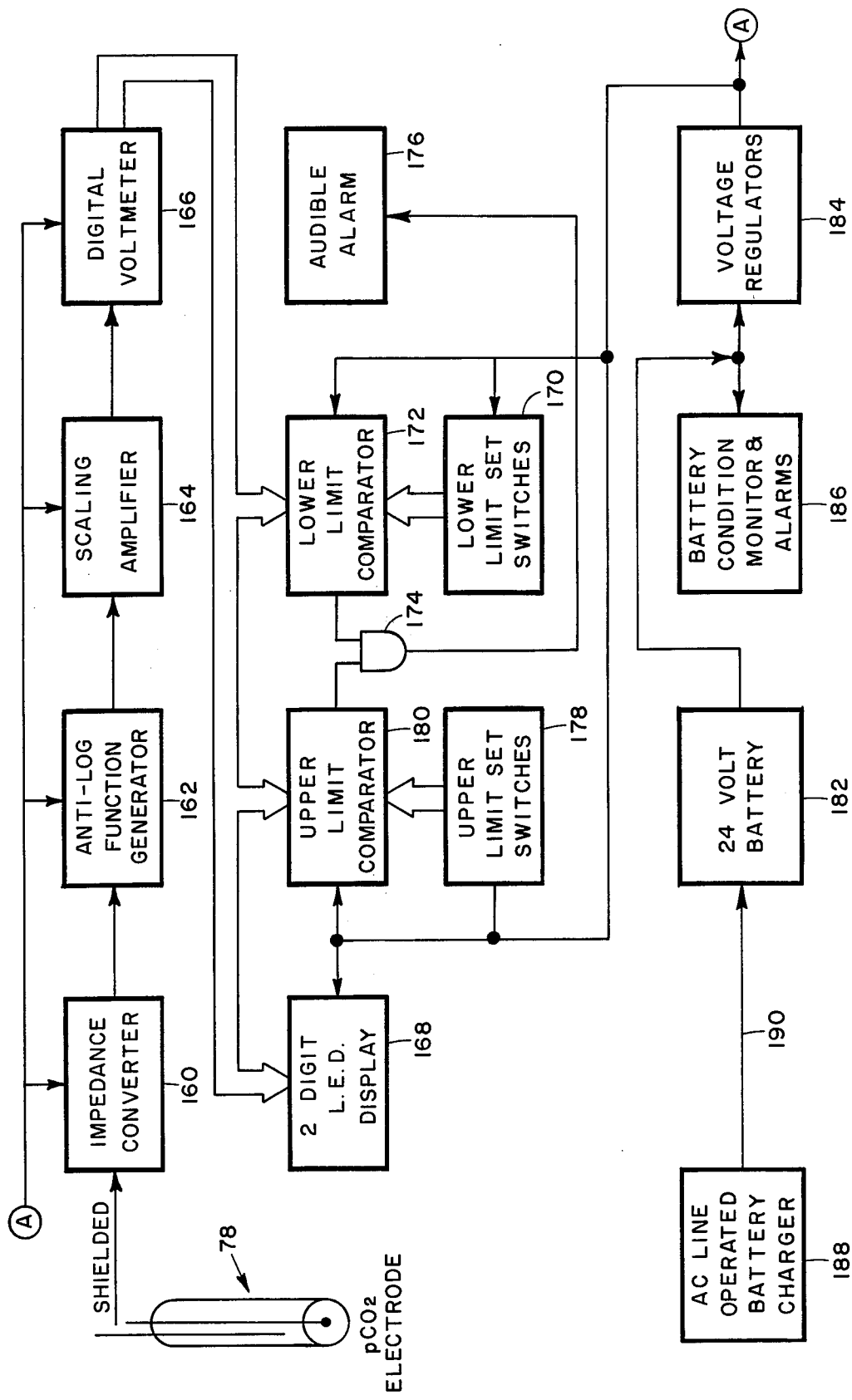
FIG. 7 is a schematic block diagram of an analyzer circuit for the $CO_2$ electrode.

The operation of the $CO_2$ electrode 78 as it is used to regulate the anesthesia breathing circuit will be explained in more detail herein in conjunction with FIG. 7. The $CO_2$ electrode 78 is a standard type that may be purchased commercially which has a semi-permeable membrane that will not allow liquids to penetrate, but gas, including exhaled carbon dioxide, will penetrate. Voltage developed across the $CO_2$ electrode 78 gives a very high impedance output of the order of $10^{12}$ to $10^{14}$ ohms. The connection from the $CO_2$ electrode 78 to an impedance converter 160 is shielded to prevent any outside interference. In fact, inside of the impedance converter 160 shielding is still used until the impedance of the signal from the $CO_2$ electrode 78 has been changed to a more usable form. Even the shielding is isolated to prevent the pickup of unwanted noise or interference. The impedance converter 160 may use different types of isolation devices, including field effect transistors, as a means for reducing the impedance of the signal down to a more usable form. Also, by having adjustable operational amplifiers as a part of the impedance converter 160, the circuit as shown in FIG. 7 can be calibrated. By immersing the $CO_2$ electrode 78 into a gas having a known value, a low calibration point of the impedance converter 60 is set by a first external adjustment thereto. Next, by immersing the $CO_2$ electrode 78 in a known gas of a higher carbon dioxide content, a high calibration for the impedance converter 160 is also set by a second external adjustment thereto.

An output signal from the $CO_2$ electrode 78 after being converted through the impedance converter 160 feeds to an analog function generator 162. The analog function generator 162 produces a nonlinear analog relationship between the input and output. The nonlinear analog relationship is necessary because the voltage developed by the $CO_2$ electrode 78 versus the tension of $CO_2$ is a logarithmic relationship. Therefore, it is necessary to generate an analog function thereby converting the signal received from the $CO_2$ electrode 78 through the impedance converter 160 to a generally linear relationship.

The output signal from the analog function generator 162 is fed to a scaling amplifier 164. The scaling amplifier 164 produces a signal of a more convenient size that may be used by the digital voltmeter 166. Also, the scaling amplifier 164 has an external adjustment that may be used to compensate for temperature and other variables as may exist between the carbon dioxide received in the control module 10 and the carbon dioxide tension as exists in the patient's bloodstream. This adjustment has been determined experimentally as will be described hereinafter.

The output signal from the digital voltmeter 166 is fed to a two digit light emitting diode display 168 that gives the $CO_2$ tension as measured by the $CO_2$ electrode 78. To insure that the $CO_2$ as measured by the $CO_2$ electrode 78 is within certain limits, a lower limit set switch 170 feeds a lower limit voltage level into lower limit comparator 172, which lower limit voltage level is representative of the minimum value of $CO_2$ that should exist in the control module 10 as measured by the $CO_2$ electrode 78. If the value being fed into the lower limit comparator 172 from the digital voltmeter 166 is less than the value being fed into the lower limit comparator 172 by the lower limit set switch 170, an output signal will feed through OR gate 174 to operate an audible alarm 176.

Likewise, the upper limit set switch 178 feeds a predetermined voltage level into upper limit comparator 180 that is representative of a maximum value of $CO_2$ that should exist in the control module 10 as measured by the $CO_2$ electrode 78. If the output for the digital voltmeter 166 exceeds the value set by the upper limit set switch 178 as fed into the upper limit comparator 180, the upper limit comparator 180 will feed an output signal through OR gate 174 to audible alarm 176. Naturally, the voltage levels of upper limit set switch 178 and lower limit set switches 170 may be varied according to the patient's changed conditions.

The circuit as just described in FIG. 7 is designed for operation off of a 24 volt rechargable battery 182. The power used to drive the electronics for the $CO_2$ analyzer circuit as shown in FIG. 7 is provided by the 24 volt battery 182 via voltage regulator 184. The output voltage from voltage regulator 184 provides power for the previously described components of FIG. 7. If the voltage for the 24 volt battery 182 drops below a predetermined level, battery condition monitor and alarm 186 will give an output signal indicating the charge of the 24 volt battery 182 has dropped below a predetermined level. An AC line operated battery charger 188 may be connected to the 24 volt battery 182 by means of a detachable cord 190. Once the 24 volt battery 182 is brought to a predetermined charge level, the AC line operated battery charger 188 is disconnected and removed.

In order to calibrate the $CO_2$ analyzer circuit shown in FIG. 7, the $CO_2$ electrode 78 is placed in a calibration chamber, such as elongated housing 28 or other suitable enclosure. Next, for example, a predetermined percent carbon dioxide gas (such as 5% $CO_2$) is connected to the calibration chamber. The low calibration of the impedance converter 160 is adjusted so that the two digit light emitting diode display 168 gives the proper readout. For instance, the proper readout on the two digit light emitting diode display 168 is "37", which is determined by multiplying 5% times the ambient barometric pressure (740 millimeters of mercury). The value 37 is equal to 37 millimeters of mercury or "37 torr". Next, by connecting a different value of $CO_2$ gas to a calibration chamber (such as 10% $CO_2$), the impedance converter 160 is adjusted through its high calibration. By multiplying 10% times the ambient barometric pressure, a reading of 74 millimeters of mercury should be shown on the display 168. The calibration as just described can also be performed when the $CO_2$ electrode 78 is inserted into the control module 10.

After the control module 10 has been flushed with a fresh gas and stabilized after connection to the patient, an additional calibration in the scaling amplifier 164 is necessary. It has been found through experimentation that for a normal adult, after the monitoring of the expired carbon dioxide inside of the control module 10 has stabilized, that a positive adjustment of approximately 5 millimeters of mercury must be made in the scaling amplifier 164 to properly reflect the carbon dioxide tension in the bloodstream of the patient. Therefore, if the patient after stabilization had an indication of 40 millimeters of mercury on display 168, the scaling amplifier 164 would be adjusted so that the display 168 would indicate 45 millimeters of mercury. This adjustment is probably necessary to compensate for the differences in temperature, as well as numerous other factors, and has been experimentally derived to more closely correlate the readout of the display 168 to the arterial blood carbon dioxide tension. This correlation is usually within a range of plus or minus 2 millimeters of mercury of the actual arterial carbon dioxide tension. The compensating factor, as adjusted into the scaling amplifier 164, adjusts the difference between the actual arterial carbon dioxide tension and that read by the $CO_2$ electrode 78 in the control module 10 of the breathing circuit.

By use of a breathing circuit having the control module 10 as previously described, a patient's carbon dioxide tension can be continuously monitored. As a patient's carbon dioxide tension increases, a change in the fresh gas flow to the patient will cause a reciprocal change in the carbon dioxide tension as indicated by the display 168. As a patient's expired carbon dioxide tension changes, it is sensed almost immediately by the carbon dioxide electrode 78.

The present anesthesia breathing circuit is designed so that it can be completely disassembled and reconnected according to the particular requirements. Each of the components of the anesthesia breathing system may be sterilized, including the control module 10. All of the components connected to the control module 10 can be quickly disconnected therefrom and individually sterilized, as well as the control module 10. The inhalation breathing circuit 90 may either be sterilized or discarded and replaced with a new circuit. The versatility of the controllable partial rebreathing circuit is its most desirable feature. When the control module 10 is used, the $CO_2$ electrode 78 and analyzer circuit becomes very important in continually maintaining a desirable carbon dioxide tension in the patient. Various safety features as associated with the control module 10 prevent accidental overpressurization of the patient, or creating of a vacuum that would prevent the delivery of fresh gases to the patient. These and many other features are incorporated as part of the anesthesia breathing circuits previously described and shown in conjunction with FIGS. 2 and 4.

Figure 8:
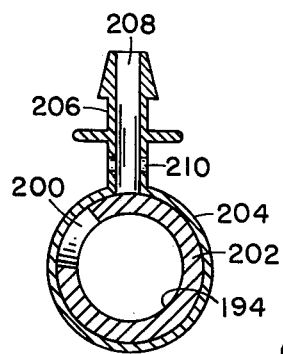
FIG. 8 is a cross-sectional view of FIG. 5 taken along section lines 8—8.

In FIGS. 2 and 3, the inhalation breathing circuit 90 may be removed from the bacterial filter 92 and/or control module flange 12 and connected to a reservoir bag 152 with the exhaust control valve 192 interposed for providing continuous ventilatory support when transporting a patient from the operating theater to the surgical recovery area. The exhaust control valve 192 can be seen in more detail in the cross-sectional view of FIGS. 5 and 8. Passage 194 of the exhaust control valve 192 is in flow communication with passage 186 of circuit connector 94 and reservoir bag 152. One end of the exhaust control valve 192 is received in large opening 96 of the circuit connector 94, and the other end of control valve 192 is received in opening 198 of the reservoir bag 152. A wedge-shaped opening 200 is provided in the wall 202 of passage 194. Encircling wall 202 to cover wedge-shaped opening 200 is a ring 204. Radial stem 206 is connected to ring 204 and has an opening 208 extending therethrough. By adjustment of the ring 204, opening 208 overlaps with wedge-shaped opening 200 to allow expired gases to escape. The wedge-shaped feature of opening 200 allows for regulation of the expired gases.

A vacuum line can be connected to radial stem 206 to scavenge the mixed expired gases. Side ports 210 in radial stem 206 would prevent a vacuum from being created in the inhalation breathing circuit 90. Also, a bacterial filter 92 may be included as part of the inhalation breathing circuit 90.

By use of the inhalation breathing circuit 90, anesthesia reservoir bag 152, and/or exhaust control valve 192, a patient may be ventilated during transportation from one location to another while fresh gases are still being received through the small tube 104. The use of an anesthesia reservoir gag 152 is necessary on many occasions for short periods of time. If, during transportation of the patient, suctioning or observation with a fiberoptic bronchoscope is necessary, plug 132 may be removed and the suctioning tube or bronchoscope inserted through upper opening 132. By having a tight connection with upper opening 132, the normal ventilation of the patient can continue.

METHOD OF USING THE APPARATUS

Prior to anesthetizing a patient with the invention, the carbon dioxide analyzer control circuit shown in FIG. 7 is calibrated by placing the $CO_2$ electrode 78 in a calibration chamber or in the elongated housing 28. A predetermined percentage of carbon dioxide gas (calibration gas) is connected to the calibration chamber or elongated housing 28 through the auxiliary conduit 34. This is usually a low concentration gas (frequently 5% $CO_2$). The low calibration of the impedance converter 160 in FIG. 7 is adjusted to readout on the two digit light emitting diode display 168 the partial pressure of the carbon dioxide in the calibrating gas. This partial pressure is independently determined by multiplying 5% times the ambient barometric pressure (for example, 740 millimeters of mercury). No correction is necessary for water vapor since the gases are used dry. The resultant value of 37 millimeters of mercury or torr is set on the two digit light emitting diode display 168 using impedance converter 160.

Next, by connecting a different calibration carbon dioxide gas (such as 10% $CO_2$) to the calibration chamber or auxiliary conduit 34, the impedance converter 160 is adjusted through its high calibration observing the readout on the two digit light emitting diode display 168. This reading, attached by multiplying barometric pressure (740 millimeters of mercury) times 10% $CO_2$ should read 74 millimeters of mercury or torr. These steps may be rechecked to assure correct calibration.

At this point, using the scaling amplifier 164, the reading on the two digit light emitting diode 168 is advanced 5 millimeters of mercury or torr in the positive direction. That is to say, if the $CO_2$ analyzer has been calibrated and the reading on the two digit light emitting diode display is 74 (with 10% $CO_2$ gas in the calibration chamber), the scaling amplifier 164 is turned until the reading is now 79. This step is performed to compensate for an experimentally derived figure of approximately 5 torr, expressing the difference between arterial carbon dioxide tension and mixed expired carbon dioxide tension. This later step, using the scaling amplifier 164, may be performed with the $CO_2$ electrode 78 in the circuit provided the readings are relatively stable during calibration.

Once the $CO_2$ analyzer is calibrated and inserted into the control module 10, the entire circuit is pressurized by allowing fresh gas to flow into the circuit through fresh gas flow line 138. Also, the exhalation/scavenger valve 42 is closed, and the patient opening of the elbow adapter 128 is manually sealed. By observing the pressure reading on the pressure gauge 14, the pressure relief governor/alarm valve 20 may be set by adjusting nut 60 to relieve pressure in excess of a predetermined amount and provide an alarm.

With the $CO_2$ analyzer and pressure relief governor/alarm 20 calibrated, the $O_2$ analyzer with oxygen sensor 24 (if used) may be calibrated in the standard manner while inserted into the control module 10.

After inspecting the entire anesthesia circuit and anesthesia machine as is routinely done prior to administration of anesthesia, the anesthesia circuit is ready for use.

If administration of gases with the anesthesia circuit is accomplished according to the method previously described by Rayburn, the following calculations are usually made prior to the onset of administration of gases. Using the patient's height and weight determined in the usual manner, the patient's surface area as expressed in square meters is obtained from a nomogram or surface area calculator. Having obtained this surface area value, it is multiplied by an experimentally derived constant of 2500 ml/m$^2$/min. The resultant value is the total fresh gas flow delivered through the fresh gas line 138 via metering valve 140, into the small tube 104 and hence into the entire anesthesia circuit. This fresh gas flow will maintain the arterial carbon dioxide tension at approximately 40 torr, provided minute ventilation is at least three (3) times the fresh gas flow. The minute ventilation, which may be provided using either a mechanical ventilator 86 or manual ventilation using a reservoir bag 152, may be provided by using any one of a number of combinations of respiratory rate and tidal volume relationships totalling a value three times the fresh gas flow. This is true provided the tidal volume is not decreased to a point that normal alveolar minute ventilation is not maintained. For example, using a 10 kilogram child whose surface area is 0.5 m², the fresh gas flow rate delivered through fresh gas line 138 is 1250 ml/min. The minute ventilation is three times this value, or 3750 ml/min. The tidal volume delivered by the mechanical ventilator 86 or by manual ventilation using reservoir bag 152 to the patient's lungs through the distal aperture in expiratory mixing tube connector 114 is usually set at 15 ml/kg. The respiratory rate is then calculated by dividing the tidal volume into the minute ventilation (i.e. 3750 ml/min÷150 ml=25 breaths/min).

Having made these calculations, the patient may be connected to the controllable partial rebreathing anesthesia circuit for administration of gases, by any means deemed suitable for controlled ventilation. Fresh gas flow through fresh gas line 138 is set according to the above calculations using metering valve 140. The minute ventilation, either from the ventilator bellows 144 through ventilator delivery hose 88 into the circuit or from the reservoir bag 152, is set using the above calculations for minute ventilation. Under these conditions, after a short time for equilibration of patient and anesthesia circuit, the carbon dioxide analyzer should read on the two digit light emitting diode display 168, a number very near 40 torr, which correlates closely with the arterial blood gas carbon dioxide tension. If the number on the two digit light emitting diode display 168 is significantly larger than 40, an increase in the fresh gas flow through fresh gas line 138 is necessary in order to return the value on the two digit light emitting diode display 168 to approximately 40 torr, and assure normocapnia. If the number on the two digit light emitting diode display 168 is less than 40 torr, then less fresh gas flow is necessary. Using this method during administration of gases provides a constant monitoring of, and gives ability to change, arterial carbon dioxide tensions using a non-invasive technique.

Additional benefits derived during administration of gases by the above method centers around the greater mixing of gases and therefore, rebreathing of mixed gases. This provides greater heat and humidity retention with humidity in the large corrugated plastic tube 100 being rebreathed. The greater mixing of gases allows lower fresh gas flow than prior systems thereby providing greater economy of gases. In addition to monitoring mixed expired carbon dioxide tension in the control module 10, oxygen content and ventilating pressure are monitored using an oxygen sensor 24 and pressure gauge 14, respectively. The pressure relief governor/alarm valve 20, calibrated as described earlier, is available as a safety feature should the safe upper level of pressure be exceeded in the circuit. The exhalation/scavenger valve 42 may be used to remove and scavenge expired gases from the control module 10 when a ventilator is not being employed.

Usually the controllable partial rebreathing anesthesia circuit in pediatric patients is connected via the terminal port of the expiratory mixing tube connector 114. Use of the elbow adapter 128 in small patients may increase the arterial and mixed expired carbon dioxide tensions due to dead space. If the elbow adapter 128 is used in small patients, then a porportional increase in fresh gas flow over that calculated must be delivered through the fresh gas line 138 to maintain the carbon dioxide tension at 40 torr.

The inhalation breathing circuit 90 may be removed from the control module 10 and attached to the exhaust control valve 192 and reservoir bag 152 for delivery of gases by controlled or spontaneous ventilation. This may be used for transport of patients, respiratory care, resuscitation, or delivery of anesthetic gases. In the case of controlled ventilation, ventilation may be provided by opening and closing the exhaust control valve 192 in order to provide manual ventilation via reservoir bag 152. A bacterial filter 92 may be connected between the circuit connector 94 and the exhaust control valve 192. Fresh gas flow may be delivered through fresh gas line 138 to small tube 104 using the previously stated calculations provided minute ventilation is unchanged. This respiratory assist device is suitable generally for short procedures and those procedures involving spontaneous ventilation.

We claim:

1. In an anesthesia rebreathing system including means for administering a mixture of fresh gases and patient expired gases to a patient wherein said fresh gases are comprised of anesthesia gas and/or oxygen and are delivered via a fresh gas supply line, the system comprising:
   a first tube having a first end connected to said fresh gas supply line and a second end;
   a second tube having an unobstructed flow path and having first and second ends and being concentric with said first tube, said first and second tubes having said second ends terminating immediately adjacent each other;
   adapter means for connecting said second ends of said first and second tubes to a first end thereof, a second end of said adapter means being constructed and arranged to connect to either an endotracheal tube or breathing mask of said patient, said second tube mixing said fresh gases from said first tube with expired gases from said patient;
   module means connected to said first end of said second tube for receiving said mixture of fresh and expired gases therein;
   means for removing a predetermined portion of said mixture of said gases from said module means and away from said anesthesia rebreathing system;
   means for transferring said mixture of gases from said module to said patient via said second tube;
   measuring means in said module means for determining carbon dioxide tension of said mixture of fresh and expired gases; and
   control means for proportionate adjustment of fresh gases fed to said patient as a function of said carbon dioxide tension measured in said mixture of said fresh and expired gases.

2. The system of inhalation anesthesia as given in claim 1 comprising means for measuring oxygen content of said mixture of gases in said module means.

3. The system of inhalation anesthesia as given in claim 2 comprising means for limiting pressure of said mixture of gases in said module means, warning means being operable by said limiting means to indicate if preset pressure limits have been exceeded.

4. The system of inhalation anesthesia as given in claim 1 wherein said adapter means is constructed and arranged so that said first and second tubes connect to said adapter means at approximately ninety degrees to any endotracheal tube that may be connected thereto, said adapter means having removable plug means for allowing essentially straight entry into said endotracheal tube to said patient's lungs while continuously supplying said fresh gases to said patient.

5. The system of inhalation anesthesia as given in claim 4 comprising circuit connector means having large longitudinal passage therethrough, said second tube connecting to said large longitudinal passage, said circuit connector means having a small passage connected to said longitudinal passage at an acute angle, said first tube extending into said longitudinal passage and out said small passage for an externally visible connection with said fresh gas supply line, said first tube being bent to an obtuse angle as it extends through said small package.

6. The system of inhalation anesthesia as given in claim 1 comprising bacteria filter means in said second tube for filtering said mixture of gases prior to being received in said module means.

7. The system of inhalation anesthesia as given in claim 1 wherein both said means for removing and said means for transferring comprises a mechanical ventilator connected to said module means.

8. The system of inhalation anesthesia as given in claim 1 wherein said removing means includes adjustable valve means to control said removal of said mixture of gases from said module means, and means associated with said adjustable valve means adaptable for scavenging by a vacuum source.

* * * * *